(12) United States Patent
Chen et al.

(10) Patent No.: US 7,847,128 B2
(45) Date of Patent: Dec. 7, 2010

(54) PROCESS FOR PRODUCING CYCLOHEXYLBENZENE

(75) Inventors: Tan-Jen Chen, Kingwood, TX (US); Jane C. Cheng, Bridgewater, NJ (US); Terry E. Helton, Bethlehem, PA (US); John Scott Buchanan, Lambertville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/663,303

(22) PCT Filed: Aug. 12, 2008

(86) PCT No.: PCT/US2008/072843

§ 371 (c)(1), (2), (4) Date: Dec. 7, 2009

(87) PCT Pub. No.: WO2009/038900

PCT Pub. Date: Mar. 26, 2009

(65) Prior Publication Data

US 2010/0179351 A1 Jul. 15, 2010

Related U.S. Application Data

(60) Provisional application No. 60/974,312, filed on Sep. 21, 2007.

(30) Foreign Application Priority Data

Jan. 21, 2008 (EP) .................................. 08001564

(51) Int. Cl.
*C07C 45/27* (2006.01)
*C07C 37/08* (2006.01)
*C07C 2/68* (2006.01)
*C07C 15/067* (2006.01)

(52) U.S. Cl. ...................... 568/361; 568/798; 585/446; 585/467

(58) Field of Classification Search ................. 568/361, 568/798; 585/446, 467
See application file for complete search history.

(56) References Cited

U.S. PATENT DOCUMENTS

| 3,760,017 | A | * | 9/1973 | Arkell et al. ................. 585/268 |
| 4,094,918 | A | | 6/1978 | Murtha et al. |
| 4,122,125 | A | | 10/1978 | Murtha et al. |
| 4,177,165 | A | | 12/1979 | Murtha et al. |
| 4,206,082 | A | | 6/1980 | Murtha et al. |
| 5,053,571 | A | | 10/1991 | Makkee |
| 6,037,513 | A | | 3/2000 | Chang et al. |
| 6,489,529 | B1 | * | 12/2002 | Cheng et al. ................. 585/471 |
| 6,506,953 | B1 | * | 1/2003 | Cheng et al. ................. 585/269 |
| 6,730,625 | B1 | * | 5/2004 | Chang et al. ................... 502/66 |

FOREIGN PATENT DOCUMENTS

EP 0 338 734 10/1989

\* cited by examiner

*Primary Examiner*—Sikarl A Witherspoon

(57) ABSTRACT

In a process for producing cyclohexylbenzene, benzene and hydrogen are fed to at least one reaction zone. The benzene and hydrogen are then contacted in the at least one reaction zone under hydroalkylation conditions with a catalyst system comprising a molecular sieve having an X-ray diffraction pattern including d-spacing maxima at 12.4±0.25, 6.9±0.15, 3.57±0.07 and 3.42±0.07 Angstrom, and at least one hydrogenation metal to produce an effluent containing cyclohexylbenzene. The catalyst system has an acid-to-metal molar ratio of from about 75 to about 750.

16 Claims, No Drawings

PROCESS FOR PRODUCING CYCLOHEXYLBENZENE

CROSS-REFERENCE TO RELATED APPLICATIONS

This application is a National Stage Application of International Application No. PCT/US2008/072843 filed Aug. 12, 2008, which claims priority from EP 08001564.7 filed Jan. 21, 2008, which claims priority from U.S. Ser. No. 60/974,312 filed Sep. 21, 2007, all of which are incorporated herein by reference.

FIELD

The present invention relates to a process for producing cyclohexylbenzene and optionally for converting the resultant cyclohexylbenzene into phenol and cyclohexanone.

BACKGROUND

Phenol is an important product in the chemical industry and is useful in, for example, the production of phenolic resins, bisphenol A, $\epsilon$-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene. Thus, a process that uses higher alkenes instead of propylene as feed and coproduces higher ketones, rather than acetone, may be an attractive alternative route to the production of phenols.

For example, oxidation of cyclohexylbenzene (analogous to cumene oxidation) could offer an alternative route for phenol production without the problem of acetone co-production. This alternative route co-produces cyclohexanone, which has a growing market and is used as an industrial solvent, as an activator in oxidation reactions and in the production of adipic acid, cyclohexanone resins, cyclohexanone oxime, caprolactam and nylon 6. However, this alternative route requires the development of a commercially viable process for producing the cyclohexylbenzene precursor.

It has been known for many years that cyclohexylbenzene can be produced from benzene by the process of hydroalkylation or reductive alkylation. In this process, benzene is heated with hydrogen in the presence of a catalyst such that the benzene undergoes partial hydrogenation to produce cyclohexene which then alkylates the benzene starting material. Thus U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffer from the problems that the selectivity to cyclohexylbenzene is low, particularly at economically viable benzene conversion rates, and that large quantities of unwanted by-products, particularly cyclohexane and methylcyclopentane, are produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof and the contacting step is conducted at a temperature of about 50 to 350° C., a pressure of about 100 to 7000 kPa, a benzene to hydrogen molar ratio of about 0.01 to 100 and a WHSV of about 0.01 to 100. The '513 patent discloses that the resultant cyclohexylbenzene can then be oxidized to the corresponding hydroperoxide and the peroxide decomposed to the desired phenol and cyclohexanone.

According to the present invention, it has now been found that when a bifunctional catalyst comprising an aluminosilicate molecular sieve of the MCM-22 family and a hydrogenation metal is used to effect hydroalkylation of benzene, the catalyst exhibits enhanced selectivity to monocyclohexylbenzene and reduced selectivity to dicyclohexylbenzene and cyclohexane, when the acid-to-metal molar ratio (defined as the number of moles of the aluminum in the molecular sieve to the number of moles of the hydrogenation metal) of the catalyst is from about 75 to about 750.

SUMMARY

In one aspect, the invention resides in a process for producing cyclohexylbenzene, the process comprising:

(a) feeding benzene and hydrogen to at least one reaction zone;

(b) contacting the benzene and hydrogen in said at least one reaction zone under hydroalkylation conditions with a catalyst system comprising an aluminosilicate molecular sieve having an X-ray diffraction pattern including d-spacing maxima at 12.4±0.25, 6.9±0.15, 3.57±0.07 and 3.42±0.07 Angstrom, and at least one hydrogenation metal to produce an effluent containing cyclohexylbenzene, wherein the catalyst system has an acid-to-metal molar ratio (defined as the number of moles of the aluminum in the molecular sieve to the number of moles of the hydrogenation metal) of from about 75 to about 750.

Conveniently, the catalyst system has an acid-to-metal molar ratio of from about 100 to about 300.

Conveniently, the molecular sieve is selected from MCM-22, PSH-3, SSZ-25, ERB-1, ITQ-1, ITQ-2, MCM-36, MCM-49, MCM-56, UZM-8, and mixtures of any two or more thereof, and especially MCM-22, MCM-49, MCM-56 and isotypes thereof.

Conveniently, said at least one hydrogenation metal is selected from palladium, ruthenium, nickel, zinc, tin, and cobalt, especially palladium.

In one embodiment, at least 50 wt %, more preferably at least 75 wt %, and most preferably substantially all (even 100 wt %), of said at least one hydrogenation metal is supported on an inorganic oxide different from said molecular sieve, such as an oxide of one of Groups 2, 4, 13 and 14 of the Periodic Table of Elements. Such oxide preferably comprises alumina and/or titania and/or zirconia.

Conveniently, the hydroalkylation conditions include a temperature in the range of about 100 to 400° C. Conveniently, the hydroalkylation pressure is in the range of about 100 to 7000 kPaa.

In a further aspect, the invention resides in a method for coproducing phenol and cyclohexanone, the method comprising producing cyclohexylbenzene by the process described herein, oxidizing the cyclohexylbenzene to produce cyclohexylbenzene hydroperoxide and cleaving the cyclohexylbenzene hydroperoxide to produce phenol and cyclohexanone.

DETAILED DESCRIPTION

Described herein is a process for the hydroalkylation of benzene to produce cyclohexylbenzene and then the conversion of the cyclohexylbenzene in a two step process to cyclohexanone and phenol. Insofar as the hydroalkylation step produces dicyclohexylbenzene in addition to the desired monocyclohexylbenzene product, the process can include the further step of transalkylating the dicyclohexylbenzene with additional benzene to produce additional monocyclohexylbenzene product.

Benzene Hydroalkylation

The first step in the present process comprises contacting benzene with hydrogen under hydroalkylation conditions in the presence of a hydroalkylation catalyst whereby the benzene undergoes the following reaction to produce cyclohexylbenzene (CHB):

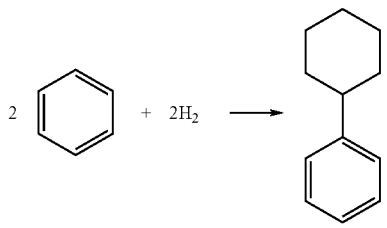

Competing reactions include the complete saturation of the benzene to produce cyclohexane, dialkylation to produce dicyclohexylbenzene and reorganization alkylation reactions to produce impurities, such as methylcyclopentylbenzene (MCPB). Although dicyclohexylbenzene can be transalkylated to produce additional CHB product, conversion to cyclohexane represents loss of valuable feed, whereas impurities such as methylcyclopentylbenzene (MCPB) are particularly undesirable since the boiling point of MCPB is very close to that of CHB so that it is very difficult to separate MCPB from CHB. It is therefore important to maximize the selectivity to cyclohexylbenzenes in the hydroalkylation reaction.

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Preferably, the total feed to the hydroalkylation step contains less than 1000 ppm, such as less than 500 ppm, for example less than 100 ppm, water. Preferably, the total feed typically contains less than 100 ppm, such as less than 30 ppm, for example less than 3 ppm, sulfur. Preferably, the total feed contains less than 10 ppm, such as less than 1 ppm, for example less than 0.1 ppm, nitrogen. In a particularly preferred embodiment at least two, and preferably all three of the above mentioned preferred levels for water, sulfur and nitrogen are achieved.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Generally, the ratio of the total number of moles of hydrogen fed to the reaction to the number of moles of benzene fed to the reaction is between about 0.15:1 to about 15:1, for example from about 0.3:1 to about 1:1, such as between about 0.4:1 and about 0.9:1. Suitable temperatures for conducting the hydroalkylation reaction are between about 100° C. and about 400° C., such as between about 125° C. and about 250° C. Suitable reaction pressures are between about 100 and about 7,000 kPaa, such as between about 500 and about 5,000 kPaa.

The catalyst employed in the hydroalkylation reaction is a bifunctional catalyst comprising an aluminosilicate molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures of any two or more thereof. Preferably, the molecular sieve is selected from (a) MCM-49, (b) MCM-56 and (c) isotypes of MCM-49 and MCM-56, such as ITQ-2.

Any known hydrogenation metal can be employed in the present hydroalkylation catalyst although suitable metals include palladium, ruthenium, nickel, zinc, tin, and cobalt, with palladium being particularly advantageous. In particular, the amount of hydrogenation metal present in the catalyst is selected such that the molar ratio of the aluminum in the molecular sieve to the hydrogenation metal is from about 75 to about 750, such as from about 100 to about 300.

The hydrogenation metal may be directly supported on the (MCM-22 family) molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina and/or titania and/or zirconia. As used herein, the numbering scheme for the Periodic Table Groups is as disclosed in Chemical and Engineering News, 63(5), 27 (1985). When the catalyst system comprises a composite of the aluminosilicate molecular sieve and the inorganic oxide that is different from the molecular sieve, these two components are conveniently present in a weight ratio in the range 90:10 to 10:90, such as 80:20 to 20:80, for example 70:30 to 30:70 or 60:40 to 40:60.

In the above-mentioned preferred embodiment, the hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain some dialkylated products, as well as unreacted aromatic feed and the desired monoalkylated species. The unreacted aromatic feed is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y or mordenite. The transalkylation reaction is typically conducted under at least partial liquid phase conditions, which suitably include a temperature of about 100 to about 300° C. and/or a pressure of about 800 to about 3500 kPa and/or a weight hourly space velocity of about 1 to about 10 $hr^{-1}$ on total feed and/or a benzene/dicyclohexylbenzene weight ratio about of 1:1 to about 5:1.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2dicarboximide, N-hydroxynaphthalimide sodium salt or N-hydroxy-o-benzenedisulphonimide. Preferably, the catalyst is N-hydroxyphthalimide. Another suitable catalyst is N,N',N"-trihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 mol % to 15 wt %, such as between 0.001 to 5 wt %, of the cyclohexylbenzene.

Suitable conditions for the oxidation step include a temperature between about 70° C. and about 200° C., such as about 90° C. to about 130° C. and/or a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase. This is conveniently carried out at a temperature of about 20° C. to about 150° C., such as about 40° C. to about 120° C. and/or a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species.

The following Example is given for illustrative purposes and does not limit the scope of the invention.

Example 1

To illustrate the importance of acid/metal ratio in hydroalkylation over MCM-22 family molecular sieves, back-to-back experiments were conducted on two catalysts prepared identically except for the acid/metal ratio. Both of these catalysts contained 2 g of 0.3 wt % Pd supported on gamma alumina. The Pd/Al$_2$O$_3$ hydrogenation catalyst was then co-pelletized with HMCM-49 aluminosilicate molecular sieve (silica to alumina molar ratio of 18). The main difference between catalyst A and catalyst B (see Table 1) was that the former contained 1.6 g MCM-49 catalyst whereas the latter contained 4.8 g MCM-49. The molar ratio of the aluminum in MCM-49 to Pd was 50 for catalyst A. The corresponding ratio for catalyst B was 150.

Catalysts A and B were tested under nominally identical conditions. The benzene feed rate was 0.08 cc/min while the hydrogen feed rate was 10 cc/min. The reaction temperature was 150° C. while the pressure was 1034 kPag (150 psig). The results are summarized in Table 1.

TABLE 1

| Catalyst | A | B |
| --- | --- | --- |
| Acid/metal molar ratio | 50 | 150 |
| Conversion, wt % | 43.5 | 42.5 |
| Selectivity, wt % | | |
| Cyclohexane | 7.1 | 3.2 |
| Cyclohexylbenzene | 70.8 | 78.0 |
| Dicyclohexylbenzene | 17.3 | 13.8 |
| Others | 4.8 | 5.0 |

As can be seen from Table 1, the performance of catalyst B was superior to the performance of catalyst A. The conversion of both catalysts was comparable (42 versus 43 wt % conversion) but the total selectivity towards cyclohexylbenzene and dicyclohexylbenzene was nearly 92 wt % for catalyst B which was significantly higher than the selectivity of 88% for catalyst A. In addition, catalyst B was significantly more selective towards monocyclohexylbenzene than catalyst A (78 wt % versus 70.8 wt %).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing cyclohexylbenzene, the process comprising:
   (a) feeding benzene and hydrogen to at least one reaction zone;
   (b) contacting the benzene and hydrogen in said at least one reaction zone under hydroalkylation conditions with a catalyst system comprising an aluminosilicate molecular sieve having an X-ray diffraction pattern including d-spacing maxima at 12.4±0.25, 6.9±0.15, 3.57±0.07 and 3.42±0.07 Angstrom, and at least one hydrogenation metal to produce an effluent containing cyclohexylbenzene, wherein the catalyst system has an acid-to-metal molar ratio of from 75 to 750.

2. The process of claim 1, wherein the catalyst system has an acid-to-metal molar ratio of from 100 to 300.

3. The process of claim 1, wherein the molecular sieve is selected from MCM-22, PSH-3, SSZ-25, ERB-1, ITQ-1, ITQ-2, MCM-36, MCM-49, MCM-56, UZM-8, and combinations of any two or more thereof.

4. The process of claim 3 wherein the molecular sieve is selected from MCM-22, MCM-49, MCM-56 and combinations of any two or more thereof.

5. The process of claim 1, wherein the at least one hydrogenation metal is selected from palladium, ruthenium, nickel, zinc, tin, and cobalt.

6. The process of claim 5 wherein the hydrogenation metal comprises palladium.

7. The process of claim 1, wherein at least 50 wt % of the hydrogenation metal is supported on an inorganic oxide different from the molecular sieve.

8. The process of claim 7 wherein at least 75 wt % of the hydrogenation metal is supported on the inorganic oxide.

9. The process of claim 8 wherein substantially all of the hydrogenation metal is supported on the inorganic oxide.

10. The process of claim 7 wherein the at least one hydrogenation metal is applied to the inorganic oxide before the inorganic oxide is composited with the molecular sieve.

11. The process of claim 7 wherein the inorganic oxide comprises an oxide of at least one element of Groups 2, 4, 13 and 14 of the Periodic Table of Elements.

12. The process of claim 11 wherein the inorganic oxide comprises alumina and/or titania and/or zirconia.

13. The process of claim 1, wherein the hydroalkylation conditions include a temperature of 100 to 400° C. and/or a pressure of 100 to 7000 kPaa.

14. The process of claim 1, wherein the ratio of the total number of moles of hydrogen fed to said contacting to the number of moles of benzene fed to said contacting is between 0.15:1 and 15:1.

15. The process of claim 1, wherein the effluent also contains dicyclohexylbenzene and at least part of the dicyclohexylbenzene is contacted with benzene under transalkylation conditions to produce further cyclohexylbenzene.

16. A method for coproducing phenol and cyclohexanone, the method comprising producing cyclohexylbenzene by the process of claim 1, oxidizing the cyclohexylbenzene to produce cyclohexylbenzene hydroperoxide and cleaving the cyclohexylbenzene hydroperoxide to produce phenol and cyclohexanone.

\* \* \* \* \*